United States Patent [19]

Grey et al.

[11] Patent Number: 5,397,338

[45] Date of Patent: Mar. 14, 1995

[54] ELECTROTHERAPY DEVICE

[75] Inventors: Thomas L. Grey, Sacramento; Lawrence E. Bertolucci, Citrus Heights, both of Calif.

[73] Assignee: Maven Labs, Inc., Citrus Heights, Calif.

[21] Appl. No.: 175,650

[22] Filed: Dec. 30, 1993

Related U.S. Application Data

[63] Continuation-in-part of Ser. No. 38,179, Mar. 29, 1993, abandoned.

[51] Int. Cl.$^6$ .............................................. A61N 1/32
[52] U.S. Cl. ................... 607/115; 607/149; 607/46
[58] Field of Search ............ 607/46, 50, 74, 3, 72, 607/75, 115, 148, 149, 152; 128/639

[56] References Cited

U.S. PATENT DOCUMENTS

| | | | |
|---|---|---|---|
| 4,381,012 | 4/1983 | Russek | 607/149 |
| 4,664,118 | 5/1987 | Batters | 607/46 |
| 4,702,732 | 10/1987 | Powers et al. | 604/20 |
| 4,989,605 | 2/1991 | Rossen | 607/46 |

OTHER PUBLICATIONS

Advertisement re Neutralizer by Smith & Nephew DonJoy Inc.

Primary Examiner—George Manuel
Attorney, Agent, or Firm—Kelly, Bauersfeld & Lowry

[57] ABSTRACT

An electrotherapy device for delivering electrical energy to subcutaneous, excitable tissues in and around the joints of the human body for the purposes of pain control and the promotion of tissue healing post injury is provided. The device includes a housing containing at least one pair of electrodes connected to an electronics unit. The device is specifically designed to be small, potable and lightweight so as to not interfere with user movements and/or function. The electronics unit consists of a housing that contains batteries, a microcontroller integrated circuit (including associated control software) coupled to a transistor-based intensity stage, which is then coupled to a transformer-based output stage coupled to subminiature jacks used to connect the electronics unit to the electrodes. Control software monitors user-controlled mechanical switches for the selection of one of six operational modes (TENS, MENS, or iontophoresis) and one of six discrete intensity levels within each operational mode. The housing is a flexible, elastic sleeve that conforms to joint anatomy and has the electrodes sewn into specific positions such that when the user puts on the sleeve, the electrodes are placed at the correct anatomic position over the affected joint.

17 Claims, 4 Drawing Sheets

ELECTROTHERAPY DEVICE

This application is a continuation-in-part of application Ser. No. 08/038,179, filed on Mar. 29, 1993, now abandoned.

FIELD OF THE INVENTION

The present invention relates generally to medical devices that effectively aid in pain relief and promote healing in injured tissues using electric current. More specifically, this invention relates to the design of a single electrotherapy device that provides multiple modalities using transcutaneous electrical nerve stimulation (TENS), microcurrent electrical neuromuscular stimulation (MENS, also called microcurrent electrotherapy), and iontophoresis techniques for post-traumatic pain relief and healing.

BACKGROUND OF THE INVENTION

Transcutaneous Electrical Nerve Stimulation (TENS) has been an accepted mode of electrotherapy for many years and is well characterized (Kahn, J., *Principles and Practice of Electrotherapy*, New York, Churchill Livingstone, 1987; Greene, R. W. et al., *Transcutaneous Pain Control and/or Muscle Stimulating Apparatus*, U.S. Pat. No. 4,147,171). TENS is primarily intended for pain relief via a nerve signal blocking mechanism, but it has also been used to promote healing. TENS devices typically deliver biphasic stimulus pulses between 10 milliamperes (mA) and 100 mA in amplitude. Pulse amplitude, pulse width and pulse rate are often user adjustable. The stimulus pulse is delivered to a pair of electrodes that are manually placed over major muscle groups or nerves that are to receive the stimulation. There are several portable TENS devices available for clinical use (e.g., TENZCARE, 3M Co., St. Paul, Minn.; Premier TENS, American Imex, Irvine, Calif.; ProTENS, NTRON, Sugarland, Tex.).

Microcurrent electrotherapy, sometimes abbreviated as "MENS" (Microcurrent Electrical Neuromuscular Stimulation), is becoming a more widely accepted clinical practice for decreasing or eliminating pain and stimulating the healing process. MENS is typically used for pain relief and, more typically, for tissue healing by affecting the injured tissue at the cellular level. Tissues that respond to MENS include muscle, tendon, bone, nerve and skin. The effectiveness and use of microcurrent electrotherapy has been well documented (Wallace, L., P. T., *MENS Therapy: Clinical Perspectives*, Vol. 1, Cleveland, privately published, 1990; Picker, R. I., M.D., *Microcurrent Therapy: Harnessing the Healing Power of Bioelectricity*, (publication pending); Kahn, J., Principles and Practice of Electrotherapy, New York, Churchill Livingstone, 1987; Snyder-Mackler, L. and Robinson, A., *Clinical Electrophysiology*, Baltimore, Williams & Wilkins, 1989). However, the exact mechanisms by which microcurrent electrotherapy provides these benefits have yet to be completely characterized. MENS devices deliver a much smaller current than TENS devices (typically 20 uA (microamperes) to 600 uA). The waveforms used are typically a positive direct current (DC), negative DC or a combination of these in which the polarity is switched at an adjustable rate (usually 0.3 Hz to 30 Hz using a 50% duty cycle waveform). The use of microamperes of electrical current in MENS therapy, as opposed to TENS therapy, results in little or no patient discomfort or even sensation during application. As with TENS, electrodes must be manually placed over the tissue that is to receive the stimulation. Electrode pads are placed to follow an electrical pathway within the body, e.g., from the origin to the insertion of a muscle following muscular electrical flow, down the pathway of radiating nerve pain, through acupuncture or trigger points, or medial/lateral through a swollen joint. Sometimes electrodes are implanted into the tissue. There are currently several portable microcurrent units (a.k.a. microcurrent stimulators) available for clinical use (e.g., MENS 2000 stimulator, MONAD Corp., Pomona, Calif; PicoPulse, NAPCOR, Rancho Cucamonga, Calif.). Common user controls include amplitude (intensity), polarity and frequency.

Iontophoresis is the use of DC (as opposed to alternating or pulsed electrical currents used in microcurrent stimulators and TENS devices) to drive a charged drug into injured tissues to relieve pain and promote healing (see prior references and Nelson, R. and Currier, D., *Clinical Electrotherapy*, East Norwalk, N.J., Appleton-Century-Crofts, 1987). Iontophoresis has been shown to be a very effective modality for pain relief and tissue healing when used with appropriate pharmacologic agents (e.g., lidocaine, corticosteroids, etc.) and has been reported to affect edema by moving ions and larger, charged molecules in the blood and tissues which causes a subsequent movement of fluid. Larger currents (up to 5 milliamperes DC) are useful for fast, short-term effects, whereas smaller currents (in the hundreds of microamperes DC) are more useful for longer-term effects. As with TENS and MENS, electrodes must be manually placed over the site that is to receive the drug. However, the electrode (or skin site) must be coated with a gel or other material that holds the drug to be delivered. There are a number of commercially available, portable devices used for iontophoresis (e.g., MicroPhor and IontoPhor, Life-Tech, Inc., Houston, Tex.; TransQ and TransQ2, IOMED, Inc., Salt Lake City, Utah). User controls typically include intensity and polarity.

Current electrotherapy units have a number of characteristics that limit their functionality as an electrotherapy tool. There are several problems associated with the electrodes that are typically used. Electrodes generally require adherence to the skin with tape or an adhesive-conducting material. The tape or material often becomes loose over time rendering the electrodes and therapy ineffective. This is especially true in active patients in which the activity (e.g., passive range of motion, light exercise, normal daily activities) is prescribed as part of the overall rehabilitation therapy plan. Skin irritation may also occur with the use of these electrodes as a result of reactions to the adhesive materials used. Electrode placement is critical to effective treatment. However, patients often lack the anatomic knowledge needed to effectively place the electrodes by themselves which necessitates frequent clinic visits and limitations on therapeutic activities. The current units are about the size of a small personal radio (e.g., 3 inches wide, 4 inches long, 1 inch deep) with lead wires used to connect to the electrodes. The units are often worn on a patient's belt or in a large pocket. Problems associated with these units include: detachment of lead wires from the electrodes or stimulator during patient movements, e.g., therapeutic range of motion or exercise; interference of lead wires with daily activities; and reports of bulkiness that lead to decreased use of the stimulator unit.

Current units are also designed primarily for a single operational mode, i.e., TENS, MENS or iontophoresis. Many patients benefit from a combined therapy in which TENS, MENS and/or iontophoresis are used during different stages of therapy, which may also include the more standard interventions such as tissue compression, cold/hot treatment, passive range of motion, and exercise. The availability and use of different electrotherapy methods is often critical to treatment immediately post injury. Existing units do not promote this multi-faceted approach to injury management because they require separate devices to be available, typically with conflicting electrode requirements. Independent use of these units by a patient (per clinician instructions) as part of a complete treatment plan of managed self care is very difficult because of all the problems noted above. As such, the current units do not promote the current trend in the health care field toward managed self care.

Accordingly, there exists a need for a miniaturized, portable electrotherapy device capable of delivering multiple modes of operation, specifically TENS, MENS and iontophoresis, to an injured joint in the body for the purpose of treatment and therapy for a variety of injury-related conditions. The device must be unobtrusive and not require any parts to be adhered to the skin. It must promote proper electrode placement while being comfortable enough to be worn on the body during everyday activities. It must permit complete freedom of movement without fear that its parts will become loose or detached. The present invention fulfills these needs and provides further related advantages.

SUMMARY OF THE INVENTION

The present invention resides in an improved electrotherapy device which is miniaturized and unobtrusive while performing daily activities, and versatile offering variability in choice of mode and choice of intensity so as to be capable of treating a variety of physical conditions. The device comprises, generally, a housing containing at least one pair of electrodes connected to an electronics unit adapted for variable setting to provide electrical stimulation signals following a selected one of six different modes, each of which can be variably set in intensity.

In a preferred embodiment, the housing is a sleeve, preferably formed of a flexible elastic material such as neoprene material. The sleeve is worn around the affected joint, for example, the arm of a patient. The electrodes are carried by the sleeve for physically contacting specific musculo-tendonous structures and for therapeutic compression.

The electrodes are connected to the electronics unit by a pair of lead wires originating from at least one socket on the electronics unit. The electrodes and lead wires are sewn into the sleeve to prevent their loosening during movement. The electronics unit is connected to the sleeve by suitable fasteners.

The electronics unit contains electronic control circuit means, operating keys, at least one battery to provide the operational power supply for the invention, and an LED panel containing a plurality of LED lights which allow the user to verify the mode and intensity selected.

The control circuit means regulates operation of the electronics unit through a plurality of different modes, each mode directed to treat a specific physical condition. The control circuit means is operated by a microcontroller integrated chip, the specific design and program of which is well known to those skilled in the art. The control circuit means permits selection of signal mode and selection of intensity by manipulation of the operating keys by the user. The modes include one transcutaneous electrical nerve stimulation (TENS) mode, one of three microcurrent electrical neuromuscular stimulation (MENS) modes, and one of two iontophoretic modes.

The operating keys include a mechanical single pole dual throw switch that controls power delivered to the control circuit means by the user-changeable battery, and momentary pushbutton contact switches.

The electrode placement over precise anatomical points may be adjusted for use at anatomical sites of muscular-tendonous breakdown points surrounding the ankle, knee, hip, wrist, elbow, shoulder, neck and back.

Other features and advantages of the invention will become apparent from the following more detailed description, taken in conjunction with the accompanying drawings which illustrate by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
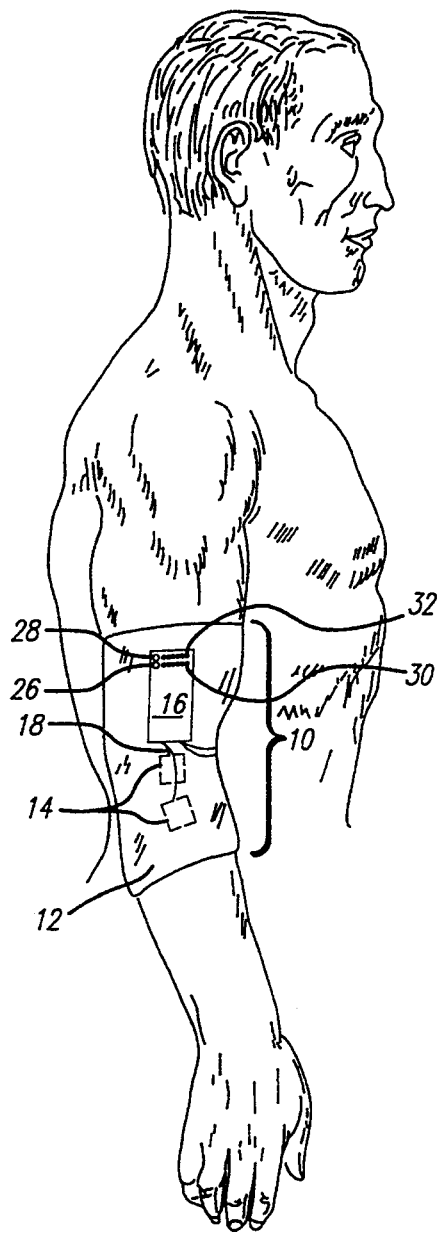
FIG. 1 is a perspective environmental view of an electrotherapy device embodying the novel features of the invention, illustrating the device worn around the arm over the elbow of a patient.
Figure 2:
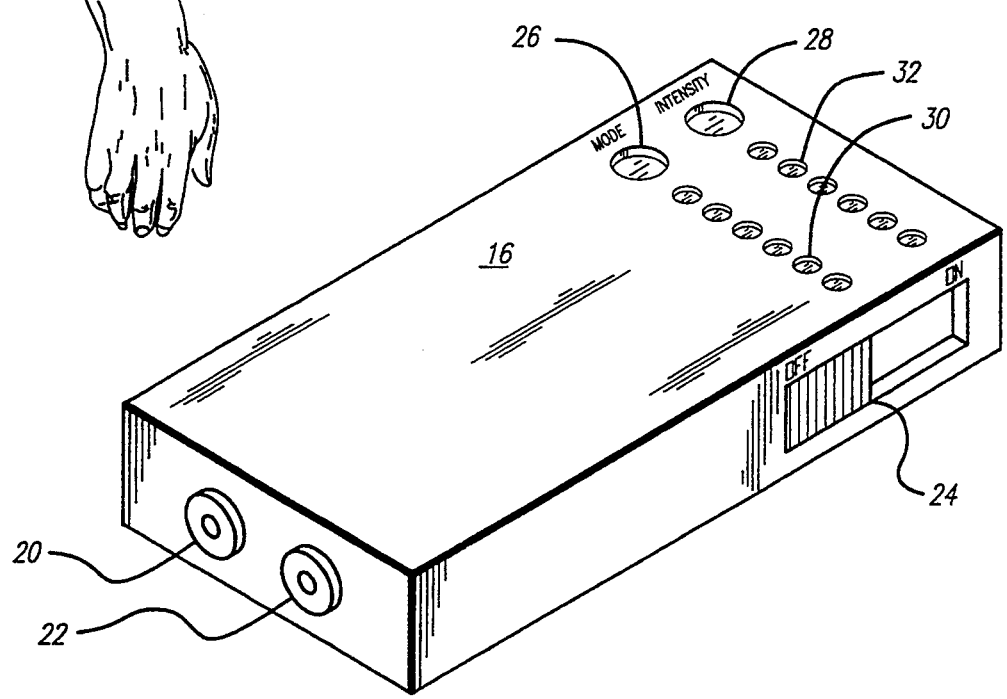
FIG. 2 is a perspective external view of an electronics unit forming a portion of the electrotherapy device.

As shown in the drawings for purposes of illustration, the present invention is concerned with an improved electrotherapy device, generally designated in the accompanying drawings by the reference number 10. The device is specifically designed to be miniaturized and self-contained and capable of effecting a plurality of different electrical modes to treat a variety of different physical conditions.

In accordance with the present invention, and as illustrated with respect to a preferred embodiment in FIGS. 1–9, the improved electrotherapy device 10 generally comprises a housing 12 containing at least one pair of electrodes 14 (typically two pair, depending on the joint to be treated), connected to an electronics unit 16 designed to provide multiple operational modes, each with discretely variable intensity.

The housing 12 in the form of a sleeve is adapted to fit around (conform anatomically to) the affected joint. The housing is preferably constructed of an elastic neoprene material which is soft and flexible allowing freedom of movement yet possessing sufficient rigidity to contain the electrodes 14 and electronics unit 16.

The elastic housing 12 has the electrodes 14 sewn into specific positions so that when the housing is worn by the user, the electrodes are placed in the correct anatomic position for optimal treatment and therapy of the affected joint as hereinafter described. FIG. 1 illustrates the sleeve worn around the elbow, but the sleeve can be shaped appropriately to be worn around, for example the wrist, ankle, or other parts of the anatomy for other treatment regimens, some of which will be described in more detail. A pair of electrode lead wires 18 connect the electrodes 14 to the electronics unit 16 at one of a pair of subminiature, two-conductor plugs 20 and 22 located at a lower end of the electronics unit 16. The lead wires 18 are also sewn into the housing 12 to prevent them from becoming loose or detached during movement. The electronics unit is securely fastened to the sleeve, e.g., by insertion into a small pocket (not shown) or by Velcro fasteners, for example. Other suitable fastening means are acceptable. The flexible, elastic housing also performs an additional therapeutic effect by being able to compress the underlying tissues by nature of the elastic material and its general shape, e.g., a sleeve, although straps with associated closures can also be sewn onto the elastic housing to promote therapeutic compression.

The electronics unit 16 is small and has a low profile housing so that it will be unobtrusive when contained in or supported by the flexible, elastic housing. An external view of the electronics unit in its preferred embodiment (FIG. 2) shows that it provides the following controls and displays to the user: the subminiature, two conductor plugs 20 and 22 for coupling to the electrodes 14 in the elastic housing 12; a mechanical single pole dual throw (SPDT) switch 24 that controls power delivered to an electronic circuit 25 (FIG. 3) by primary-type (not rechargeable) batteries 27 contained within the electronics unit 16 and changeable by the user; momentary pushbutton contact switches 26 and 28 for selecting, respectively one of six operational modes and one of six discrete intensity levels in each mode; and dual arrays of six light emitting diode (LED) indicators 30 and 32 which allow the user to respectively verify the mode and intensity selected. The user may select one TENS mode of operation, one of three microcurrent electrotherapy modes of operation, or one of two iontophoretic modes of operation (a total of six operational modes).

The stimulation signals of the various modes are illustrated in FIGS. 4–9 and are described below. Some of the descriptions are followed by references to the pertinent literature as appropriate. Peak pulse amplitudes for intensity specifications were measured using the standard American National Standards Institute (ANSI) test load using a 500 ohm series resistor in the load (see ANSI/AAMI Document NS4-1985, *American National Standard for Transcutaneous Electrical Nerve Stimulators*).

| MODE1 (FIG. 4) - TENS | |
| --- | --- |
| Application: | Pain suppression during activity or rest |
| Wavetype: | Positive Biphasic |
| Modulation: | Sinusoidal (period = 5 seconds) pulse width modulation from 60 microseconds to 170 microseconds |
| Timebase: | 80 Hz (12.5 millisecond period) |
| Intensity Settings: | LEVEL0 - zero output |
| | LEVEL1 - 10 mA peak |
| | LEVEL2 - 12 mA peak |
| | LEVEL3 - 15 mA peak |
| | LEVEL4 - 17 mA peak |
| | LEVEL5 - 20 mA peak |

(Melzack, R. and Wall, P. (Eds.), Textbook of Pain, 2d. Ed., Churchill Livingston, 1989)

| MODE2 (FIG. 5) - MENS | |
| --- | --- |
| Application: | Used during inactivity as healing mode. |
| Wavetype: | Alternating Monophasic |
| Polarity: | Polarity switched between positive and negative every 3.3 seconds |
| Timebase: | Variable duty cycle dependent on intensity selected |
| Intensity Settings: | LEVEL0 - zero output |
| | LEVEL1 - 20 microamperes DC average |
| | LEVEL2 - 40 microamperes DC average |
| | LEVEL3 - 100 microamperes DC average |
| | LEVEL4 - 250 microamperes DC average |
| | LEVEL5 - 500 microamperes DC average |

| MODE3 (FIG. 6) | |
| --- | --- |
| Application: | Used for iontophoresis with positive polarity. |
| Wavetype: | Monophasic |
| Modulation: | None |
| Polarity: | Positive |
| Timebase: | Variable, duty cycle dependent on intensity selected |
| Intensity Settings: | LEVEL0 - zero output |
| | LEVEL1 - 100 microamperes DC average |
| | LEVEL2 - 500 microamperes DC average |
| | LEVEL3 - 1 milliampere DC average |
| | LEVEL4 - 2 milliamperes DC average |
| | LEVEL5 - 4 milliamperes DC average |

| MODE4 (FIG. 7) | |
| --- | --- |
| Application: | Used for iontophoresis with negative polarity. |
| Wavetype: | Monophasic |
| Modulation: | None |
| Polarity: | Negative |
| Timebase: | Variable, depends on intensity level selected. |
| Intensity Settings: | Same as MODE3 |

| MODE5 (FIG. 8) - MENS | |
| --- | --- |
| Application: | Aids in vasoconstriction in the affected area. Effective in controlling edema and hemorrhage after injury; also used for pain relief and healing. |
| Wavetype: | Monophasic |
| Modulation: | None |
| Polarity: | Positive |

-continued

| MODE5 (FIG. 8) - MENS | |
|---|---|
| Timebase: | Variable, depends on intensity level selected |
| Intensity Settings: | LEVEL0 - zero output<br>LEVEL1 - 10 microamperes DC average<br>LEVEL2 - 20 microamperes DC average<br>LEVEL3 - 50 microamperes DC average<br>LEVEL4 - 100 microamperes DC average<br>LEVEL5 - 150 microamperes DC average |

(Nordenstrom, B, Biologically Closed Electric Circuits: Clinical, Experimental and Theoretical Evidence for an Additional Circulatory System, Nordic Medical Publications, Uppsala, 1983)

| MODE6 (FIG. 9) - MENS | |
|---|---|
| Application: | Aids in vasodialation and control of vascular system when there is chronic inflammation. |
| Wavetype: | Monophasic |
| Modulation: | None |
| Polarity: | Negative |
| Timebase: | Variable, depends on intensity selected |
| Intensity Settings:<br>(Ibid.) | Same as MODE5 |

Figure 3:
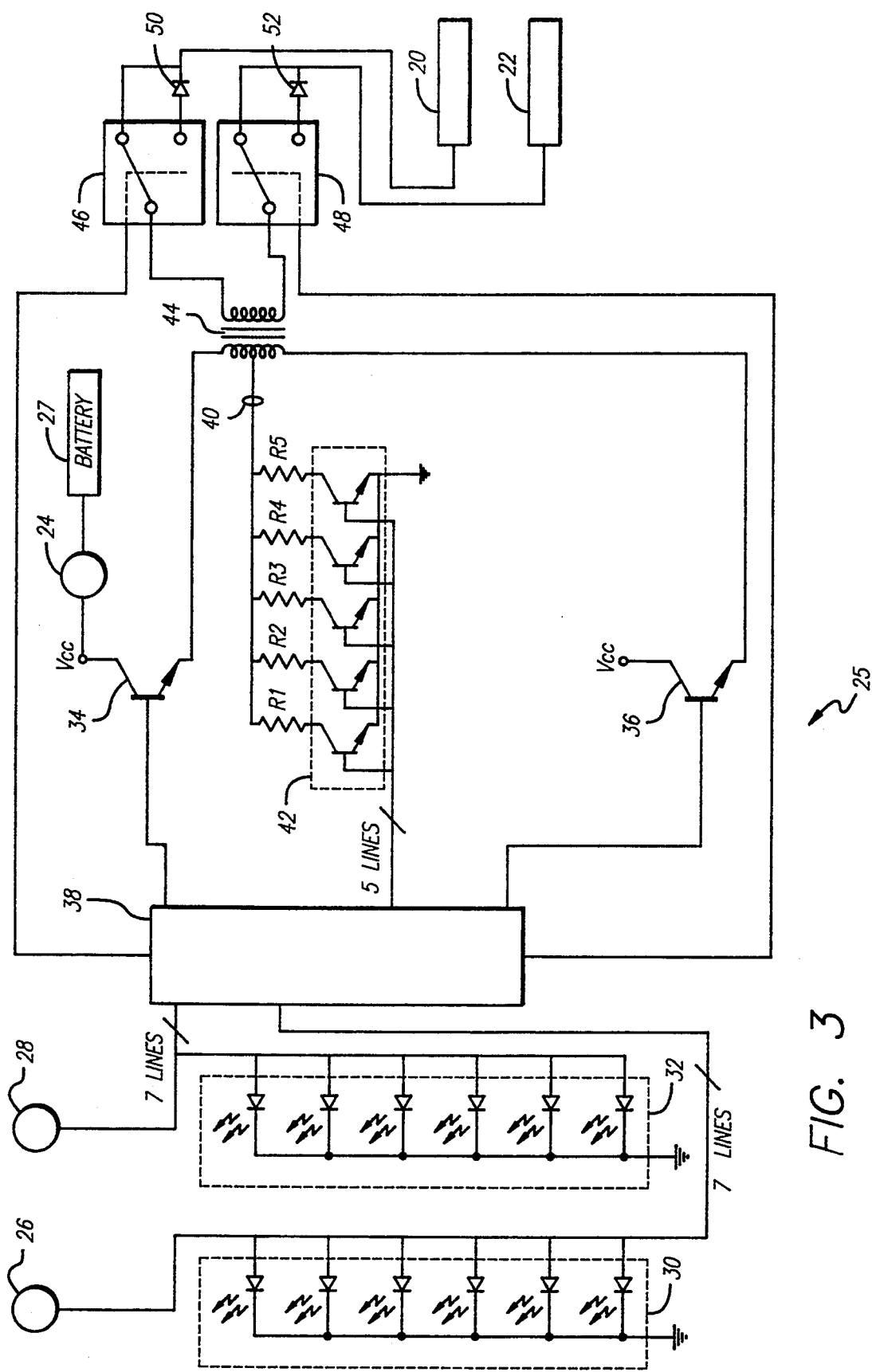
FIG. 3 is a block diagram representing an electronics circuit for the electrotherapy device.
Figure 4:
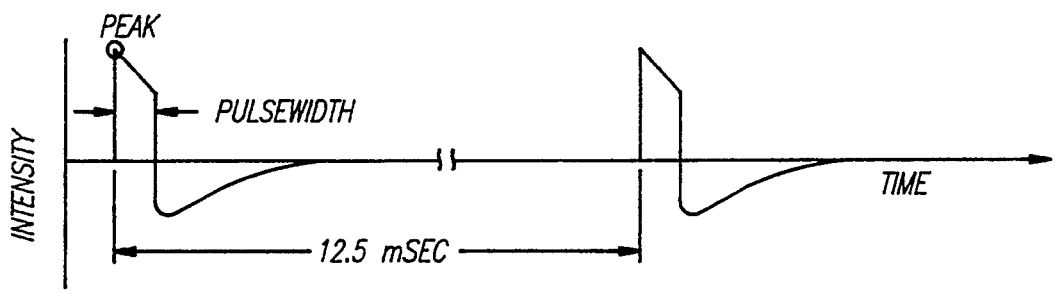
FIG. 4 is a stimulation signal diagram illustrating operation of the device in operational Mode 1.
Figure 5:
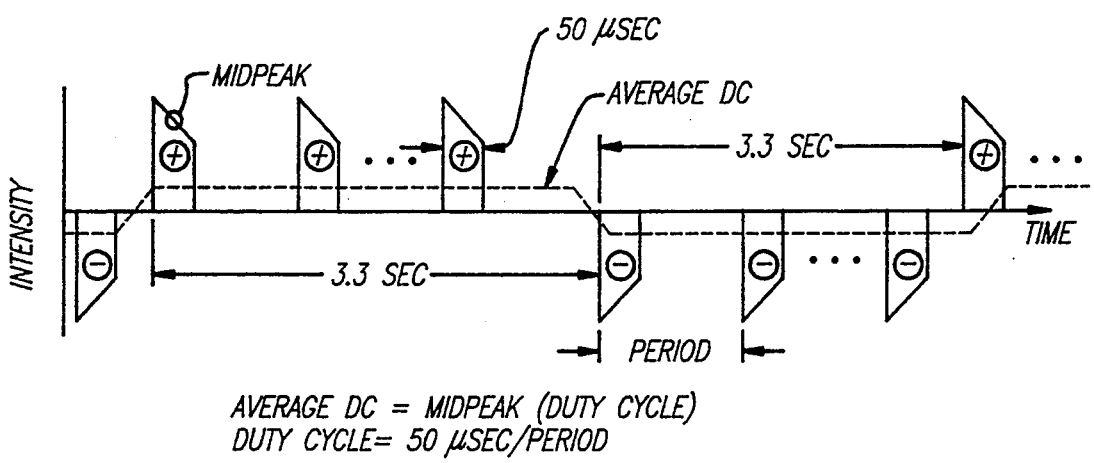
FIG. 5 is a stimulation signal diagram illustrating operation of the device in operational Mode 2.
Figure 6:
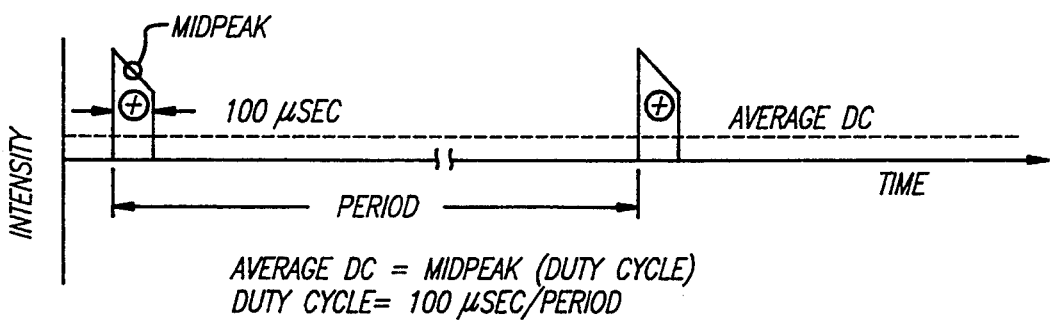
FIG. 6 is a stimulation signal diagram illustrating operation of the device in operational Mode 3.
Figure 7:
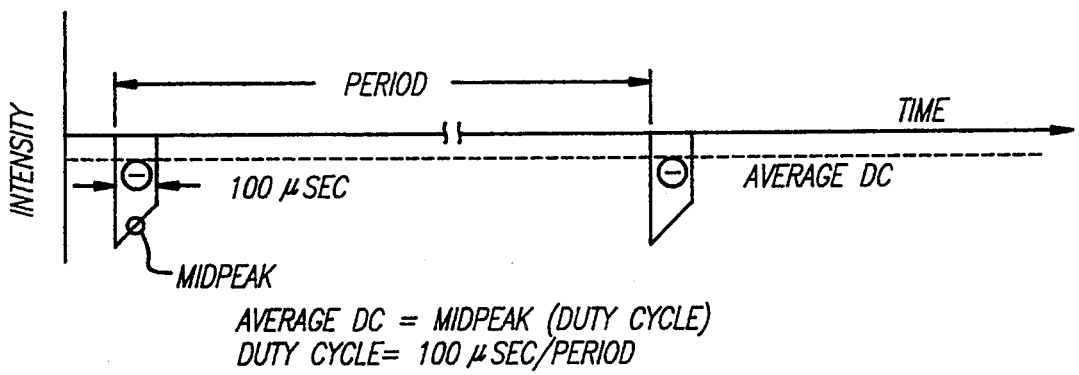
FIG. 7 is a stimulation signal diagram illustrating operation of the device in operational Mode 4.
Figure 8:
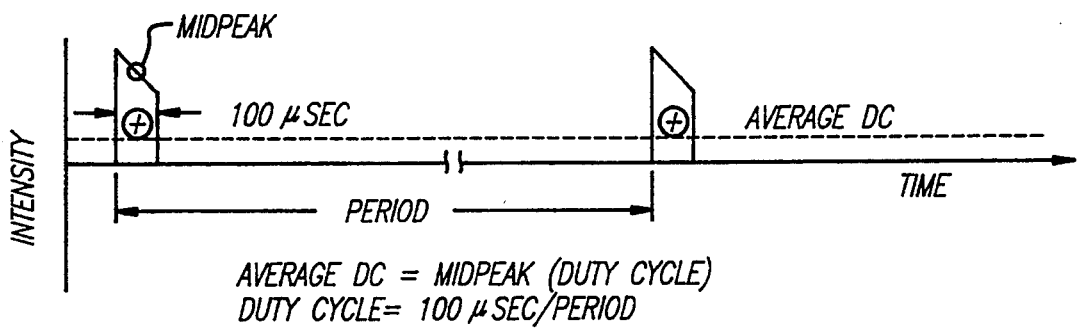
FIG. 8 is a stimulation signal diagram illustrating operation of the device in operational Mode 5.
Figure 9:
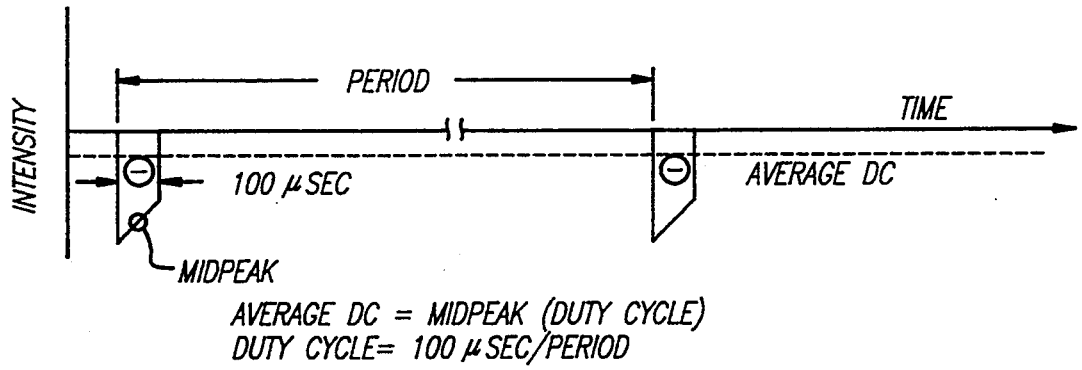
FIG. 9 is a stimulation signal diagram illustrating operation of the device in operational Mode 6.

FIG. 3 shows in block diagram form the schematic for the electronic circuit 25 of the electrotherapy device. Power is delivered to the electronic circuit by the battery 27 (e.g. 9 V) or batteries (e.g two 3 V lithium button cell batteries in series to produce 6 V). The single-pole dual-throw (SPDT) switch 24 provides an on/off function by interrupting the connection from the positive battery terminal to the electronic circuit power bus (marked as Vcc on components 34 and 36 in FIG. 3). An 8-bit microcontroller 38 provides complete control over the functioning of the electronic circuit 25 by executing a series of assembly language instructions (software) stored in programmable read-only memory within the microcontroller 38. Complete digital control over operational mode selection and intensity level selection provides a greater measure of reliability and safety than available with current TENS, MENS or iontophoresis units that provide the user with some degree of analog control (e.g. potentiometers) over operating characteristics.

The microcontroller 38 has input signals from the momentary pushbutton switches 26 and 28 which allow the user to sequentially select the operational mode and the intensity level within each of the six operational modes. The light emitting diode (LED) arrays 30 and 32 provide the user with information regarding respectively the mode and intensity that have been selected; low power (2 mA) LEDs are used to conserve battery power. During normal operation the LED correspondence to the selected mode or intensity in each array remains on until the user presses one of the pushbutton switches 26 or 28 to change either the mode or intensity.

The microcontroller 38 controls stimulus pulse frequency, duration and amplitude under the direction of the associated software. The microcontroller 38 provides a logical "high" voltage (approximately 4.8 V) to the base of either transistor 34 or transistor 36, both of which may be high current NPN or Darlington transistors, to turn the transistor on. A resistor (not shown) is placed in series at the base of each transistor to ensure that the transistor enters saturation. Transistor 34 is used to generate a positive stimulation pulse (measured at subminiature output jack 20 using subminiature jack 22 as reference). Similarly, transistor 36 is used to generate a negative stimulation pulse (measure the same as for transistor 34). Only one of these transistors is in saturation (on) at a time, and the saturated transistor serves to connect either side of a primary winding of a transformer 44 to positive voltage supply through a low resistance pathway. A centertap 40 of the transformer 44 is connected to the negative voltage supply (ground) through a parallel array of transistors 42, which are used to control the current through the transformer primary 44 to control the amplitude of the stimulus pulse. The transistor array 42 is contained in a single integrated circuit, and the transistors may be high current NPN (e.g., Harris semiconductor electronic part CA3081) or Darlington (e.g., Texas Instruments electronic part ULN2003). Only five of the transistors are used to provide five, discrete pulse amplitude (intensity) levels, but all the transistors in the array could be used to provide additional amplitude control. Each transistor in array 42 is under separate control by the microcontroller 38, and each transistor in array 42 is operated at saturation through a series resistor (not shown) at the base of each transistor in array 42. Only one transistor at a time in array 42 is placed in saturation (i.e., turned "on") by the microcontroller 38. The resistors R1 through R5 in series respectively with the collector of each array 42 transistor are selected to provide discrete steps in the peak current through the transformer 44, thus providing discrete control of the peak stimulus pulse amplitude (stimulus intensity). The values of the resistors R1 through R5 may be chosen to provide linear or nonlinear discrete changes in stimulus intensity. The resistor values were chosen to provide linear changes in stimulus amplitude with resistor R1 chosen to provide the maximum stimulus intensity and resistor R5 chosen to provide the minimum stimulus intensity. A positive stimulus pulse is generated by first turning "on" transistor 34, then one of the transistors in array 42 is turned "on" to produce a particular stimulus amplitude. Both transistors remain "on" for the duration of the stimulus, which is the pulse width. Pulse width is modulated between 60 microseconds and 170 microseconds as described below. The end of the pulse is generated by turning the array 42 transistor "off" then turning "off" transistor 34. A negative stimulus pulse is generated in a similar fashion using transistor 36. Through transformer action, a current pulse in the transformer primary winding produces a current pulse in the secondary winding, which is connected to the electrodes via subminiature jacks 20 and 22. The current pulse in the secondary winding is the stimulus pulse.

Solid state relays 46 and 48 selectively rectify the biphasic signal generated by transformer action using diodes 50 and 52 in order to produce average DC currents used in Modes 2 through 6. The solid state relay s 46 and 48 are selectively activated by the microcontroller 38. When both relays are "off" (as shown in FIG. 3), the transformer signal is not rectified for use with Mode 1. When relay 46 is "on", positive stimulus pulses are created and rectified through diode 50 to create a positive polarity average DC current by varying the duty cycle of the stimulus pulse. When relay 48 is "on" negative stimulus pulses are created and rectified through diode 52 to create a negative polarity average DC current by varying the duty cycle of the stimulus pulse. The average DC current is found using the equation Average DC=(average stimulus pulse amplitude) (duty cycle). For example, if the average pulse amplitude is 20 milliamperes (mA) and the duty cycle is 25 percent (e.g., a pulse width of 100 microseconds divided by a pulse repetition period of 400 microseconds), then the average DC current produced is (20 mA)(0.25)=5 mA. This method is used to generate the average DC currents used in Modes 2 through 6.

It is well known that excitable tissues will accommodate to stimulation unless the stimulation is modulated to prevent accommodation. Typical modulation schemes use amplitude modulation (the stimulation pulse amplitude is periodically changed while pulse duration and frequency are constant), pulse width modulation (pulse width is periodically changed while pulse amplitude and frequency are constant), or frequency modulation (pulse frequency is periodically changed while pulse amplitude and duration are constant). The modulation is typically represented by a triangle waveform, a sawtooth (repetitive ramps) waveform, or a sinusoidal waveform. This invention uses a pulse width modulation scheme in which pulse width is varied in a sinusoidal fashion from 60 microseconds to 170 microseconds. The period of the sinusoidal modulation is approximately four minutes. This modulation is used only in TENS electrotherapy modes of operation. Modulation is not provided in the microcurrent and iontophoresis electrotherapy modes in the preferred embodiment of the invention, but other embodiments of this invention may include modulation of the DC current (generated as described above) from zero DC to a specified maximum DC (e.g. 4 mA) using one of the modulation waveforms noted above for the purpose of improved drug delivery to subcutaneous tissues. The resulting current waveform would then be alternating or AC in nature, but, the term "AC current" is not used here so as to avoid confusion because that term is typically associated with the current available from a standard domestic power supply, which is typically specified as 120 VAC at 60 Hz. The rationale behind this DC current modulation is that the skin may behave like a reactive electronic component (i.e., capacitor) with regard to charged drugs being driven through the skin. The hypothesis is that a modulated DC driving current may allow more charged drugs to go through the skin than a DC driving current, much like an alternating current is more easily passed through a capacitor than a direct current. The current literature alludes to this possibility (e.g., Carley, C. et al., *An Autoregulated Pulsed-DC Mode Iontophoretic Transdermal System*, Proceedings of the 15th Annual Northeast Bioengineering Conference, Mar. 27-28, 1989, pgs. 51-52), but more clinical experimentation is required to prove or disprove the hypothesis.

The operation of the electronics unit will now be described in order to document the process followed by the control software programmed into the microcontroller 38. When the electronics unit is first turned on by switch button 24, Mode 1 and intensity LEVEL0 are set by default, and the corresponding LEDs in arrays 30 and 32 are turned on. The software polls each pushbutton switch looking for input from the user. If neither switch is pressed, the software sets the transistors and solid state relays according to the Mode and intensity LEVEL selected and generates stimulus pulses. Pressing pushbutton 26 or pushbutton 28 will cause the microcontroller 38 to cease all pulse generation (i.e. zero output), activate the next Mode or intensity LEVEL LED in sequence, and set the transistors and solid state relays accordingly. If the Mode is changed, the device automatically defaults to intensity LEVEL0, which is zero output as a safety measure. The Mode and intensity LEVEL controls incorporate a wrap-around feature. For example, if Mode 6 is currently selected and the user presses a pushbutton to change the Mode, the software changes to Mode 1. After a change has been made, the software waits one second before resuming switch polling and generation of stimulus pulses in order to give the user time to make another change.

In operation, the device can be worn around various body parts, the electrodes being placed over key anatomical structures and related acupuncture points. Various placement is described below:

Elbow:

Electrode placement will be for one pair to be placed on the lateral side of the elbow and one pair on the medial side. On the lateral side the electrode pair will be situated in the sleeve so that a first electrode will be over the insertion point of the common extensor tendons of the forearm which is the lateral epicondyle and will cover the lateral portion of the joint capsule of the radio-humeral joint and its related ligament structures; a second electrode will be placed into the sleeve so that it will be about three inches distal to the first electrode and situated over the acupuncture point of the large intestine #10. The above points will be effective in the treatment of the commonly termed medical condition "Tennis Elbow" or lateral epicondylitis, and for lateral joint sprain/strain conditions.

On the medial side the first electrode will be situated overlying the medial epicondyle and the attachment of the common flexor tendons of the forearm, the lateral joint capsule of the ulna humeral joint and its related ligaments. The second electrode will be placed approximately three inches distally and will overlie the muscle bellies of the common forearm flexors and acupuncture point small intestine #7. This pair will be utilized medically in the specific treatment of "Golfers Elbow" or medial epicondylitis problems and for medial joint sprain/strain conditions.

Wrist:

The device can be worn across the wrist for treatment of what is commonly called "Carpal Tunnel Syndrome"; or tendonitis of the wrist and finger flexor tendons as they pass through the volar retinaculum into the palm of the hand.

The specific placement of the first electrode will be directly over the proximal skin crease of the volar side of the wrist and the second electrode will be placed over the palmer surface of the hand, which will allow for deep penetration into the aponeurosis and related tendon sheaths of the long finger flexor tendons.

Shoulder:

The device can also be worn across the shoulder to treat specific joint, capsule, ligament and musculo-tendonous sprain/strain conditions. This will include the more common rotator cuff strain. There will be located two pairs of electrodes. One pair will be housed in the sleeve so that a superior/inferior orientation will occur.

The first electrode of the first pair will be placed over the anterior capsule of the shoulder also encompassing the long and short heads of the biceps and the insertion of the subscapularis tendon and the glenoid labrum. The second electrode will be housed in the sleeve so it will anatomically overlie the tendon insertions of the external rotators of the shoulder (specifically infraspinatus and teres minor muscles) and which will secondarily cover the acupuncture points of small intestine numbers 9 and 10 which are effective in the treatment of all inflammatory processes of the shoulder joint and surrounding musculature.

The second pair of electrodes will be positioned strategically in the sleeve whereby the first electrode will be over the insertion point of the deltoid muscle and corresponds with acupuncture point of large intestine #15 and the second electrode will be over the acupuncture point of large intestine #16, which is located in the depression at the intersection of the acromio-clavicular joint and the superior border of the spine of the scapular. This will also affect the musculo-tendon of the supraspinatus.

Ankle:

The device can also be worn over the ankle so as to treat joint capsular/ligamentous and musculo-tendonous sprains/strains. There will be two pairs of electrodes transfixed within the sleeve so that one pair will be lateral and one pair medial. They will be spatially oriented to cover the deep and superficial capsule/ligament and tendons as they pass anterior and posterior to the joint.

The lateral pair will be positioned so that the first electrode inserted into the sleeve will anatomically correspond over the anterior-talo-fibular ligament which is the most common ligament sprained in the ankle; and the acupuncture point of gall bladder #40. The second electrode will be positioned over the lateral posterior aspect of the fibulo-calcaneal and talar ligaments, which will secondarily also overlie the tendons of the common peroneals which are frequently injured during severe ankle and lateral foot sprains/strains.

The medial pair will be housed so as to treat the deltoid ligament of the ankle. The first electrode will be positioned to overlie the insertion point of the anterior tibialis tendon and the anterior medial joint capsule of the tibial-tolar joint. The first electrode will also cover the acupuncture point of the liver #4 and spleen #5. The second electrode will be placed posterior medially to encompass the medial/posterior attachment of the deltoid ligament and the tendons of the toe flexors and posterior tibialis and the acupuncture points of kidney numbers 3, 4, 5 and 6. This pair of electrodes will be effective in treatment of the more commonly known medical conditions of "shin splints".

Knee:

The device can be worn over the knee joint so as to treat joint, capsule, bursae, ligament and musculo-tendous sprain/strain conditions. There will be two pairs of electrodes housed within the sleeve lateral and medial. One pair will be transfixed so as to have the first electrode positioned over the lateral collateral ligament and proximal femoral attachment. The second electrode will be positioned over the distal/anterior aspect of the ligament on the fibula and the lateral aspect of the tibia; and a portion of the lateral aspect of the patella tendon; and lateral retinacula of the patella. A portion of the electrode will also encompass acupuncture point gall bladder #34.

On the medial side, the first electrode will be situated over the superior medial collateral ligament and the acupuncture point of spleen #10 and the second electrode over spleen #9, as well as the medial aspect of the patella tendon and medial/anterior aspect of the tibia catching a portion of the medial meniscus.

Back "Lumbago":

The device can be worn around the waist to assist in control of lumbar, sacro-iliac joint capsule, ligament and musculo-tendonous sprain/strain conditions.

One pair of electrodes will be positioned so as on the right and left sides of the lumbar spine adjacent to and over the transverse process of the lumbar vertebrae 1-3. The proximal electrode will extend laterally as well to encompass the attachment of the iliocostalis lumborum muscle. The electrode will also encompass the acupuncture points of bladder numbers 21 and 23.

The distal electrodes will be positioned adjacent to each other overlying acupuncture points of bladder 27 through 31. The electrode will also overlap the ligamentous structures of the ilio-lumbar, sacro-iliac, lumbo-sacral, and sacro-iliac joint and a portion of the root of the sciatic nerves bilaterally.

Neck:

The sleeve can be worn about the neck to treat sprains/strains of the cervical and cervico thoracic spine. The specific points are quite significant in the treatment of the common medical problem of "cervical whiplash" most often experienced in motor vehicle accidents. These points will also have a demonstrable effect on many headache sufferers.

There will be four electrodes, two pairs spatially oriented laterally and posterially oriented in mirror images right to left. Superiorly the proximal electrodes will be positioned to encompass two key acupuncture points bladder 10 and gall bladder 21. These two points are key in treatment of many headaches and posterior neck pain. The two distal electrodes will be positioned to cover the posterior lateral acupuncture points of small intestine #15 and gall bladder point #21. These points as the ones proximal are effective in the treatment of musculo-skeletal cervical migraine, cervical-brachial syndrome.

The device 10 of the present invention offers the patient and clinician a safe, simple and effective device for electrotherapy that does not require changing of electronic stimulation units or electrodes in order to deliver TENS, microcurrent or iontophoresis electrotherapy. The device can be worn during most daily, recreational and work activities (submersion in water is not recommended) while providing a constant level of pain relief, soft tissue support, or healing without restricting those activities. The flexible, elastic housing 12 (e.g., a sleeve for the elbow) keeps electrodes 14 in their proper position during such activities and helps prevent interruption of electrode contact with skin. The elastic housing 12 also allows introduction of conducting gel, which may also contain charged, pharmacologic agents, between the electrodes and skin. The electrodes 14, lead wires 18 and electronics unit 16 are safely contained or held into the elastic housing to avoid being pulled loose from each other. The electronic unit 16 is miniaturized to be unobtrusive. The electronics unit is also capable of effecting a variety of waveforms and intensities specifically for TENS electrotherapy, microcurrent electrotherapy and iontophoresis electrotherapy within a single unit. None of the prior art devices can accomplish such a wide variety of functions and still remain unrestrictive with regard to a patient's daily activities.

Although a particular embodiment of the invention has been described in detail for purposes of illustration, various modifications may be made without departing from the spirit and scope of the invention. Accordingly, the invention is not to be limited, except as by the appended claims.

What is claimed is:

1. An electrotherapy device for treating a variety of physical conditions comprising:
a housing having a size and shape adapted to be worn on the body;
at least one pair of electrodes carried by said housing in spaced relation to each other; control circuit means mounted within said housing and electrically coupled to said electrodes, said control circuit means having means for providing a selected simulation signal for one of a plurality of modes, each adapted for treatment of a physical condition and means for variably selecting and adjusting the intensity of said simulation signal, said modes including transcutaneous electrical nerve stimulation (TENS), microcurrent electrical nerve stimulation (MENS) and iontophoresis.

2. The electrotherapy device of claim 1, wherein said housing is an elastic flexible sleeve adapted to be worn around an affected joint of the body without impeding joint function or movement.

3. The electrotherapy device of claim 2, wherein said electrodes are carried by said sleeve for physically overlying specific musculo-tendonous structures.

4. The electrotherapy device of claim 3, wherein the affected joint is the elbow and a first pair of electrodes is positioned in the sleeve for contacting the lateral side of the elbow and a second pair of electrodes for contacting the medial side of the elbow such that a first electrode of said first pair is adapted to overlie the insertion point of the forearm common extensor tendons lateral epicondyle to cover the lateral portion of the radio humeral joint capsule, a second electrode of said first pair is about three inches distal to the first electrode and adapted to be situated over the acupuncture point of the large intestine No. 10, and a first electrode of said second pair is adapted to overlie the medial epicondyle and the attachment of the forearm common flexor tendons, the lateral joint capsule of the ulna humeral joint and its related ligaments, and a second electrode of the second pair placed about three inches distally adapted to overlie the muscle bellies of the common forearm flexors and acupuncture point small intestine No. 7.

5. The electrotherapy device of claim 3, wherein the affected joint is the wrist and a first electrode is adapted to overlie the proximal skin crease of the volar side of the wrist and a second electrode is adapted to overlie the palmer hand surface allowing for penetration into the aponeurosis and related tendon sheaths of the long finger flexor tendons.

6. The electrotherapy device of claim 3, wherein the affected joint is the shoulder and a first and second pair of electrodes is placed in the sleeve so that a superior-/inferior orientation will occur, a first electrode of said first pair adapted to overlie the shoulder anterior capsule encompassing the long and short heads of the biceps and the insertion of the subscapularis tendon and the glenoid labrum, and a second electrode of the first pair adapted to overlie the tendon insertions of the shoulder external rotators, secondarily covering the acupuncture points of small intestine Nos. 9 and 10, and a first electrode of said second pair adapted to be over the insertion point of the deltoid muscle corresponding with acupuncture point of large intestine No. 15 and a second electrode of the second pair adapted to be over the acupuncture point of large intestine No. 16.

7. The electrotherapy device of claim 3, wherein the affected joint is the ankle and a first pair of electrodes is placed in the sleeve lateral of the ankle and a second pair medial of the ankle such that a first electrode of said first pair is adapted to overlie the anterior-talo-fibular ligament and the acupuncture point of gall bladder No. 40, and a second electrode of said first pair is adapted to overlie the lateral posterior aspect of the fibulo-calcaneal and talar ligaments which secondarily overlie the tendons of the common peroneals, and a first electrode of said second pair adapted to overlie the insertion point of the anterior tibialis tendon and anterior medial joint capsule of the tibial-tolar joint also covering the acupuncture point of liver No. 4 and spleen No. 5, and a second electrode of the second pair adapted to being placed posterior medially to encompass the medial/-posterior attachment of the deltoid ligament and the tendons of the toe flexors and posterior tibialis and kidney acupuncture points 3, 4, 5 and 6.

8. The electrotherapy device of claim 3, wherein the affected joint is the knee and a first pair of electrodes is placed in the sleeve laterally and the second pair is placed in the sleeve medially, a first electrode of said first pair adapted to overlie the collateral ligament and proximal femoral attachment and a second electrode positioned over the distal/anterior aspect of the ligament on the fibula and lateral aspect of the tibia and a portion of the lateral aspect of the patella tendon and lateral retinacula of the patella and acupuncture point gall bladder No. 34 and a first electrode of said second pair over the superior medial collateral ligament and acupuncture point of spleen No. 10 and a second electrode over spleen No. 9 and the medial aspect of the patella tendon and medial anterior aspect of the tibia catching a portion of the medial menscus.

9. The electrotherapy device of claim 3, wherein the affected joint is the back and a first pair of electrodes is adapted to be positioned on the right and left side of the lumbar spine adjacent to and over the transverse process of the lumbar vertabrae 1–3, the proximal electrode extending laterally to encompass the attachment of the iliocostalis lumborum muscle and acupuncture points of bladder Nos. 21 and 23, the distal electrode adapted to be positioned adjacent to each other overlying acupuncture points of bladder Nos. 27–31, the distal electrode also adapted to overlie the ligamentous structures of the ilio-lumbar, sacro-iliac, lumbosacal, and sacroiliac joint and a portion of the sciatic nerves bilaterally.

10. The electrotherapy device of claim 3, wherein the affected joint is in the neck and a first pair of electrodes is spatially oriented laterally and posterially oriented mirror images right to left and the proximal electrodes adapted to be positioned to overlie acupuncture points bladder No. 10 and gall bladder No. 21 and the distal electrodes adapted to be positioned to overlie the posterior lateral acupuncture points of small intestine No. 15 and gall bladder No. 21.

11. The electrotherapy device of claim 3, wherein said sleeve further provides therapeutic compression of the musculo-tendonous structures.

12. The electrotherapy device of claim 1 wherein said control circuit means is user-adjustable.

13. The electrotherapy device of claim 1, wherein the user may select one TENS mode, one of three MENS modes, or one of two iontophoresis modes.

14. An electrotherapy device for delivering current to selected stimulation points on the body for relief of pain or treatment thereof, comprising:
- a sleeve adapted to be worn on the body;
- at least one pair of electrodes in spaced relation to each other carried by said sleeve to physically contact the stimulation points;
- control circuit means carried by said sleeve and electrically coupled to said electrodes, said circuit control means having mode and intensity selection means for adjustment by a patient, said mode selection means including means for providing one of a plurality of signals, wherein the signal selected is for a plurality of modes, said modes including transcutaneous electrical nerve stimulation (TENS), microcurrent electrical nerve stimulation (MENS), and iontophoresis.

15. The electrotherapy device of claim 14, wherein said intensity selection means includes means for selecting and varying the intensity of signal.

16. The electrotherapy device of claim 14 wherein said control circuit means is user-adjustable.

17. The electrotherapy device of claim 14, wherein the user may select one TENS mode, one of three MENS modes, or one of two iontophoresis modes.

* * * * *